(12) United States Patent
Dinino et al.

(10) Patent No.: US 11,607,247 B2
(45) Date of Patent: Mar. 21, 2023

(54) SYSTEM FOR MONITORING MOVEMENT OF SURGICAL INSTRUMENTS THROUGH A SURGICAL ACCESS DEVICE

(71) Applicant: Covidien LP, Mansfield, MA (US)

(72) Inventors: Matthew A. Dinino, Newington, CT (US); Roy J. Pilletere, North Haven, CT (US); Nicolette R. LaPierre, Windsor Locks, CT (US); Garrett P. Ebersole, Hamden, CT (US); Eric Brown, Madison, CT (US)

(73) Assignee: Covidien LP, Mansfield, MA (US)

( * ) Notice: Subject to any disclaimer, the term of this patent is extended or adjusted under 35 U.S.C. 154(b) by 343 days.

(21) Appl. No.: 16/836,210

(22) Filed: Mar. 31, 2020

(65) Prior Publication Data

US 2021/0298867 A1 Sep. 30, 2021

(51) Int. Cl.
| | |
|---|---|
| *A61B 17/34* | (2006.01) |
| *A61B 90/00* | (2016.01) |
| *A61B 90/50* | (2016.01) |
| *G03B 17/56* | (2021.01) |
| *A61B 1/00* | (2006.01) |

(52) U.S. Cl.
CPC ...... *A61B 17/3421* (2013.01); *A61B 1/00009* (2013.01); *A61B 17/3423* (2013.01); *A61B 90/361* (2016.02); *A61B 90/50* (2016.02); *G03B 17/561* (2013.01); *A61B 2560/0431* (2013.01)

(58) Field of Classification Search
CPC ... A61B 90/361; A61B 17/3423; A61B 90/50; A61B 2560/0431; A61B 1/00009; A61B 1/0002; A61B 1/00154; A61B 1/0684; A61B 1/3137; A61B 90/57; A61B 17/3421; G03B 17/561
See application file for complete search history.

(56) References Cited

U.S. PATENT DOCUMENTS

2020/0060724 A1 * 2/2020 Abboud ................. A61B 90/57

FOREIGN PATENT DOCUMENTS

DE 202010005202 U1 6/2010

OTHER PUBLICATIONS

European Search Report dated Aug. 5, 2021, corresponding to counterpart European Application No. 21165774.7; 7 pages.

* cited by examiner

*Primary Examiner* — Yogesh K Aggarwal
(74) *Attorney, Agent, or Firm* — Carter, DeLuca & Farrell LLP

(57) ABSTRACT

A monitoring system includes a mounting assembly for securing a recording device relative to a cannula assembly. The mounting assembly includes a cradle member configured to releasably retain the recording device and a support member including an elongate body. The elongate body has first and second ends. The first end includes a connecting portion for connecting the cradle member to the support member and the second end includes an engaging portion for securing the support member to the cannula assembly.

20 Claims, 5 Drawing Sheets

SYSTEM FOR MONITORING MOVEMENT OF SURGICAL INSTRUMENTS THROUGH A SURGICAL ACCESS DEVICE

FIELD

The disclosure relates to mounting systems for surgical access devices such as cannula assemblies. More particularly, the disclosure relates to a system for monitoring the movement of surgical instruments through a surgical access device.

BACKGROUND

In minimally invasive surgical procedures, including endoscopic and laparoscopic surgeries, a surgical access device permits the introduction of a variety of surgical instruments into a body cavity or opening. A surgical access device (e.g., a cannula or an access port) is introduced through an opening in tissue (e.g., a naturally occurring orifice or an incision) to provide access to an underlying surgical site in the body. The opening is typically made using an obturator having a blunt or sharp tip that may be inserted through a passageway of the surgical access device. For example, a cannula has a tube of rigid material with a thin wall construction, through which an obturator may be passed. The obturator is utilized to penetrate a body wall, such as an abdominal wall, or to introduce the surgical access device through the body wall, and is then removed to permit introduction of surgical instruments through the surgical access device to perform the surgical procedure.

Minimally invasive surgical procedures permit surgery to be performed on organs, tissues, and vessels far removed from an opening within the tissue. In laparoscopic procedures, the abdominal cavity is insufflated with an insufflation gas, e.g., $CO_2$, to create a pneumoperitoneum thereby providing access to the underlying organs. A laparoscopic instrument is introduced through a cannula into the abdominal cavity to perform one or more surgical tasks. The cannula may incorporate a seal to establish a substantially fluid tight seal about the laparoscopic instrument to preserve the integrity of the pneumoperitoneum. To design a robust and durable seal, information on how the seal is used (such as, for example, the speeds of inserting and removing certain surgical instruments while being manipulated through a surgical access device) would be helpful. By knowing the average/maximum speed of insertion and removal of surgical instruments, clinicians and product development teams can design devices and testing methods that correlate with real-world applications.

SUMMARY

A monitoring system for acquiring data such as recording average and maximum speeds of insertion and removal of a surgical instrument while passing through a cannula assembly is provided. The monitoring system includes a recording device, a cannula assembly, and a mounting system. The mounting system has a cradle member configured to releasably retain the recording device and a support member including an elongate body having first and second ends, the first end including a connecting portion for connecting the cradle member to the support member and the second end including an engaging portion for securing the support member to the cannula assembly.

In aspects, the recording device is configured to monitor insertion and removal of a surgical instrument through the cannula assembly.

In aspects, a camera of the recording device is aligned with an opening of the cannula assembly in such a way that the opening of the cannula assembly is disposed within a field of view of the camera.

In aspects, the camera and the opening of the cannula assembly are perpendicularly aligned.

In aspects, the connecting portion includes a first connection member configured to releasably connect to a second connection member.

In aspects, the first connection member is a male connector and the second connection member is a female connector configured to receive the male connector.

In aspects, the male connector is a T-shaped slider.

In aspects, the T-shaped slider is retained within a channel of the female connector between a stopper and a dowel pin.

In aspects, at least a portion of the engaging portion is configured to snap onto a portion of the cannula assembly or to frictionally receive at least a portion of the cannula assembly.

In aspects, the engaging portion includes a housing engaging portion and a cannula engaging portion, the housing engaging portion being configured to engage a housing of the cannula assembly and the cannula engaging portion being configured to engage a tubular member of the cannula assembly.

In aspects, the engaging portion includes at least one protrusion configured to engage the cannula assembly.

In aspects, the engaging portion defines at least one channel configured to engage a cylindrical portion of the cannula assembly.

In aspects, the at least one channel is U-shaped.

BRIEF DESCRIPTION OF THE DRAWINGS

The accompanying drawings, which are incorporated in and constitute a part of this specification, illustrate aspects of the disclosure and, together with a general description of the disclosure given above, and the detailed description of the aspects given below, serve to explain the principles of the disclosure, wherein.

DETAILED DESCRIPTION

Figure 1:
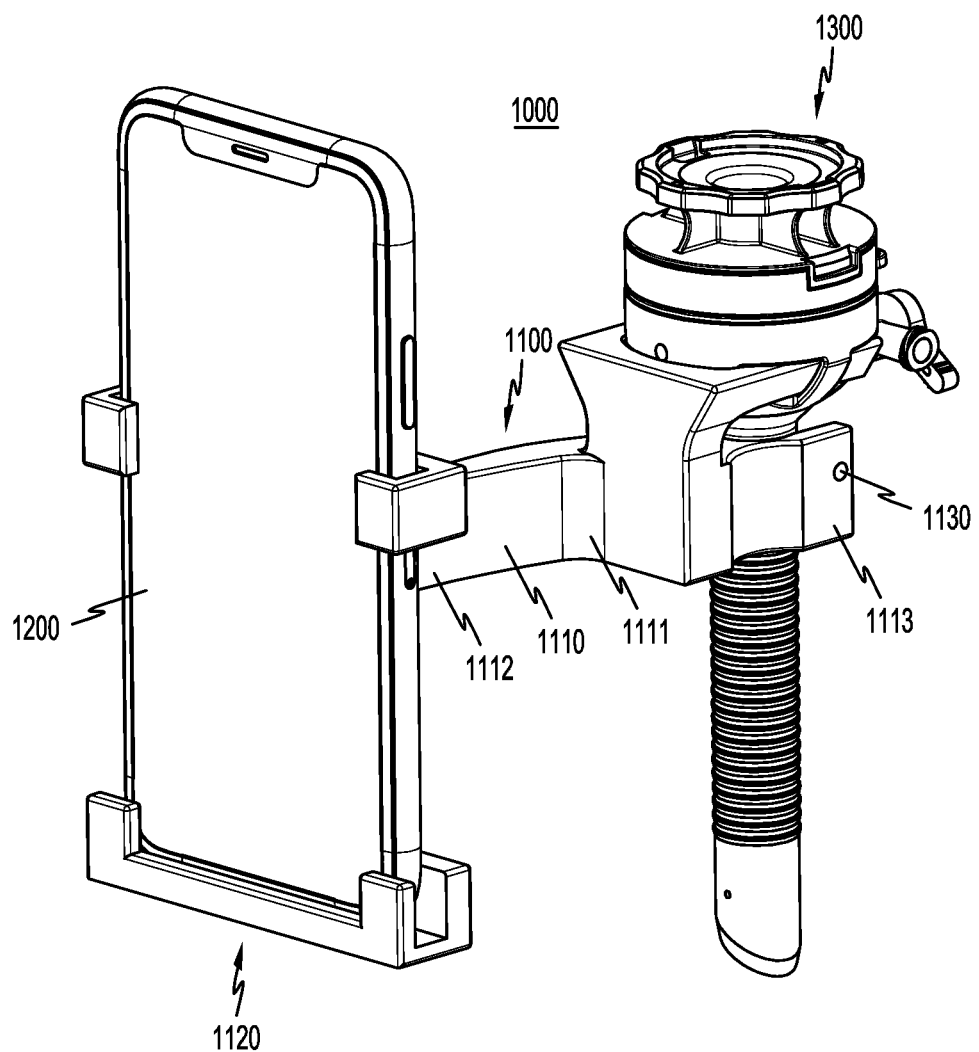
FIG. 1 is a first perspective view of a monitoring system including a mounting assembly and a recording device coupled to a cannula.

Aspects of the disclosed devices and methods for managing and monitoring the manipulation of instruments through a surgical access device or a cannula assembly are described in detail regarding the drawings in which like reference numerals designate identical or corresponding elements in each of the several views. As used herein, the term "distal" refers to that portion of the instrument, or component thereof which is farther from the user while the term "proximal" refers to that portion of the instrument or component thereof which is closer to the user. Further, to the extent consistent, any or all of the aspects detailed herein may be used in conjunction with any or all of the other aspects detailed herein.

FIG. 1 illustrates a monitoring system 1000 including a mounting assembly 1100, a recording device 1200, and a cannula assembly 1300. The monitoring system 1000 is configured to monitor a surgical instrument 10 (FIG. 6) passing through the cannula assembly 1300. The cannula assembly 1300 will only be described to the extent necessary to fully disclose the aspects of the present disclosure. For a detailed description of an exemplary cannula assembly, please refer to commonly owned U.S. Pat. Nos. 5,836,913; 8,118,305; and 10,327,809, the contents of which are hereby incorporated by reference.

Figure 2:
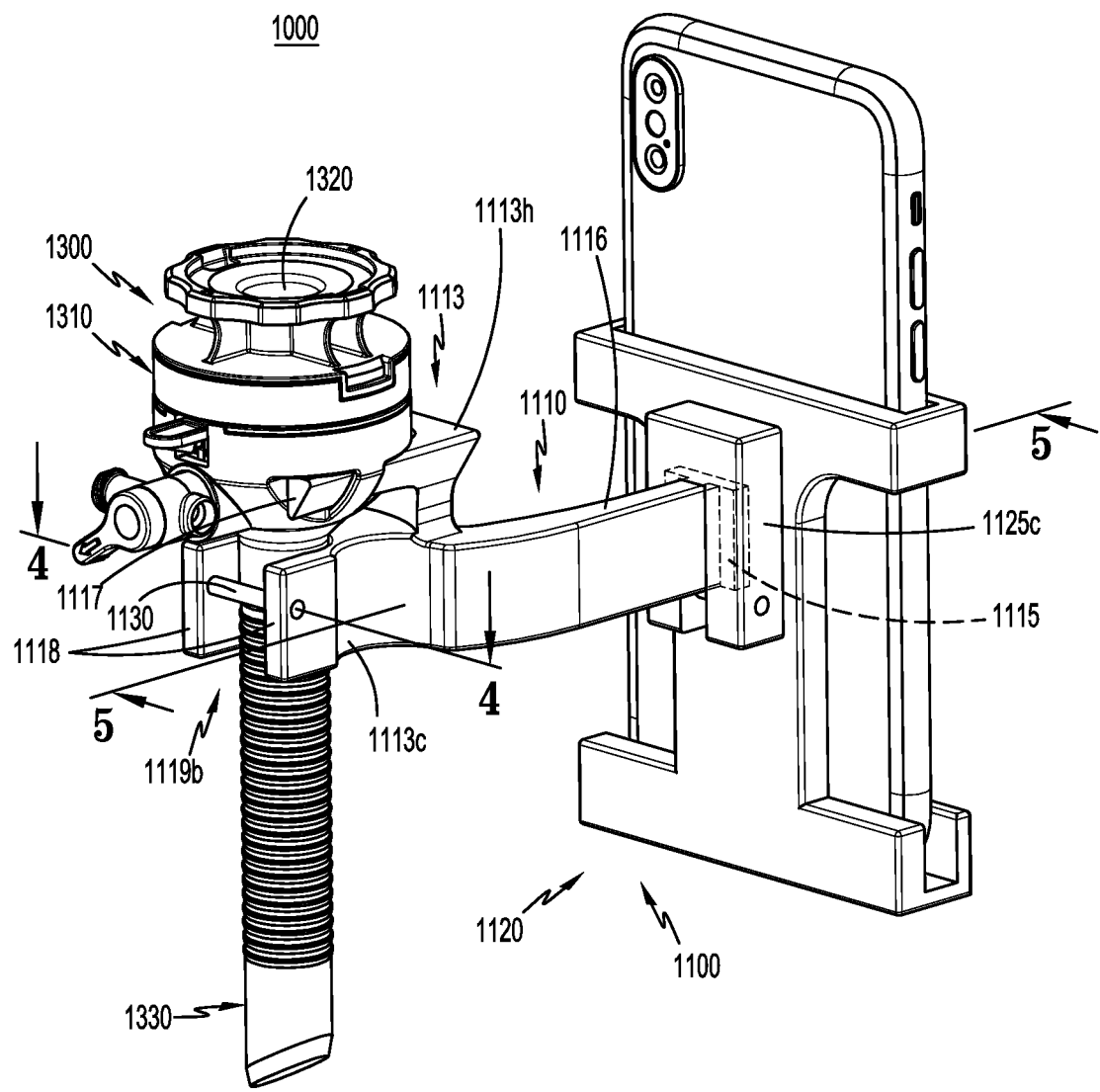
FIG. 2 is a second perspective view, opposite to the first perspective view of FIG. 1, of the monitoring system and cannula shown in FIG. 1.
Figure 3:
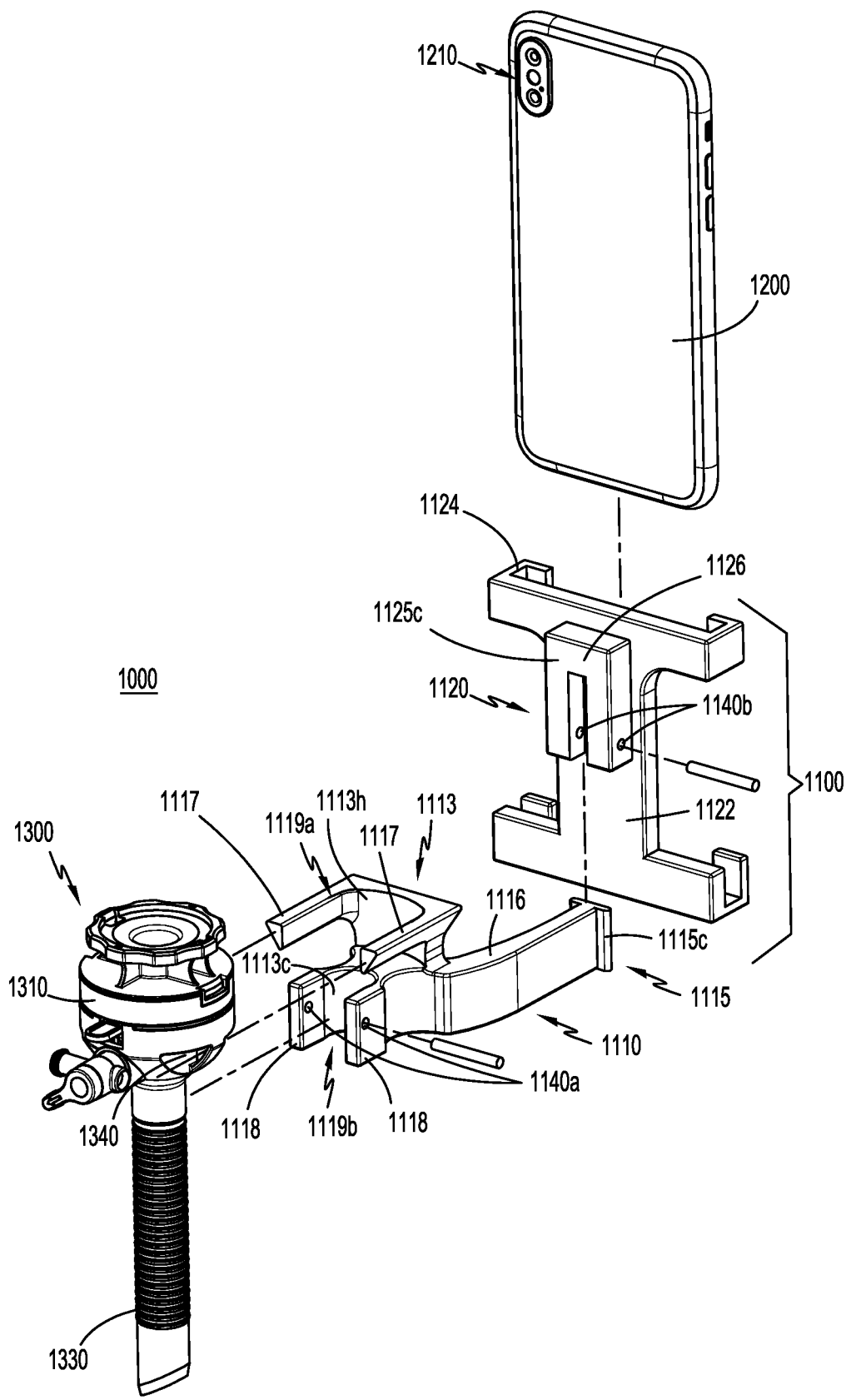
FIG. 3 is an assembly view of the monitoring system of FIG. 2, with parts separated.
Figure 8:
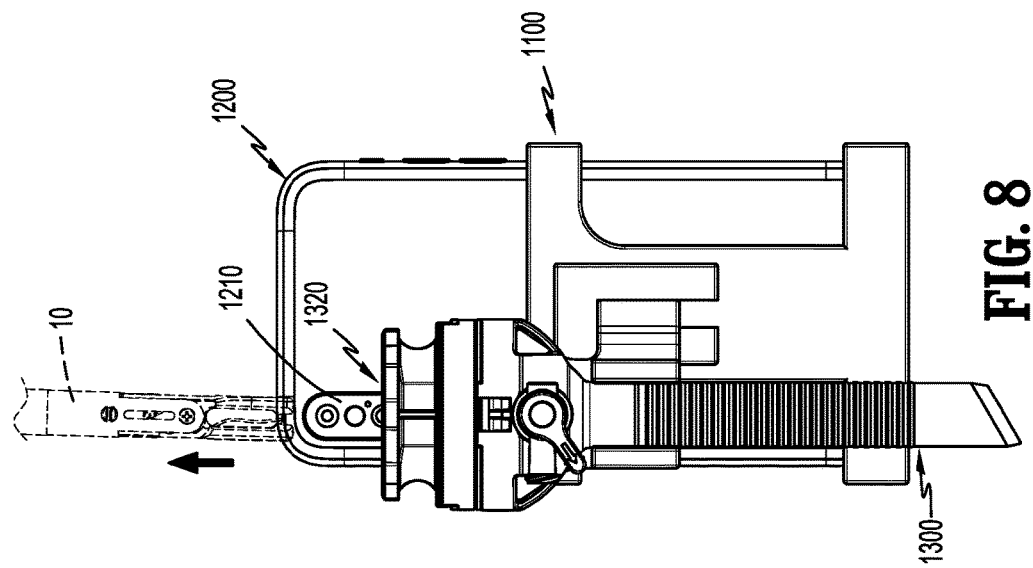
FIG. 8 is an end view of the monitoring system and cannula of FIG. 6 during removal of the instrument from the cannula.
Figure 7:
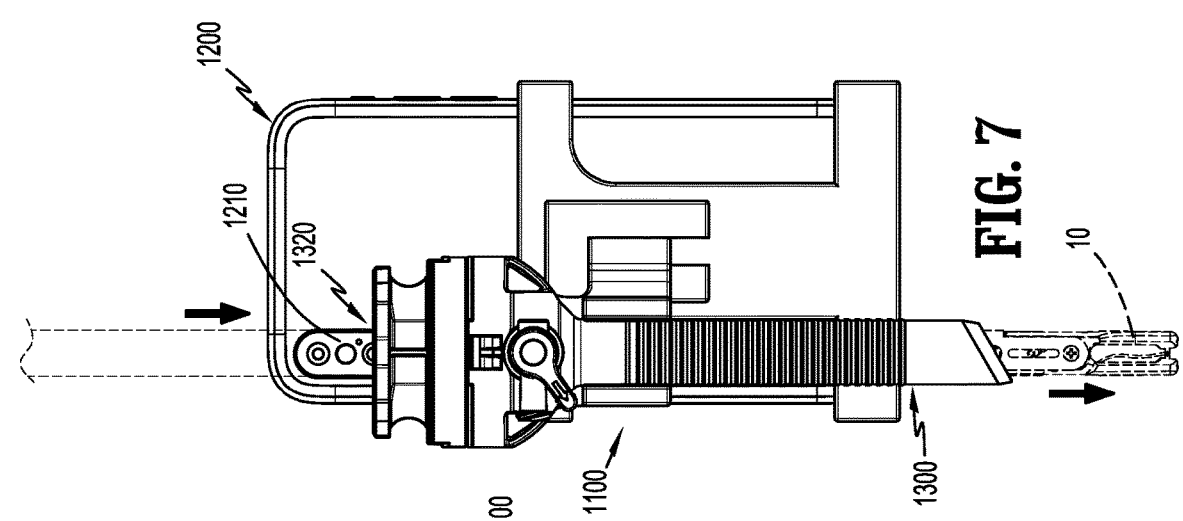
FIG. 7 is an end view of the monitoring system and cannula of FIG. 6 during insertion of the instrument through the cannula.
Figure 6:
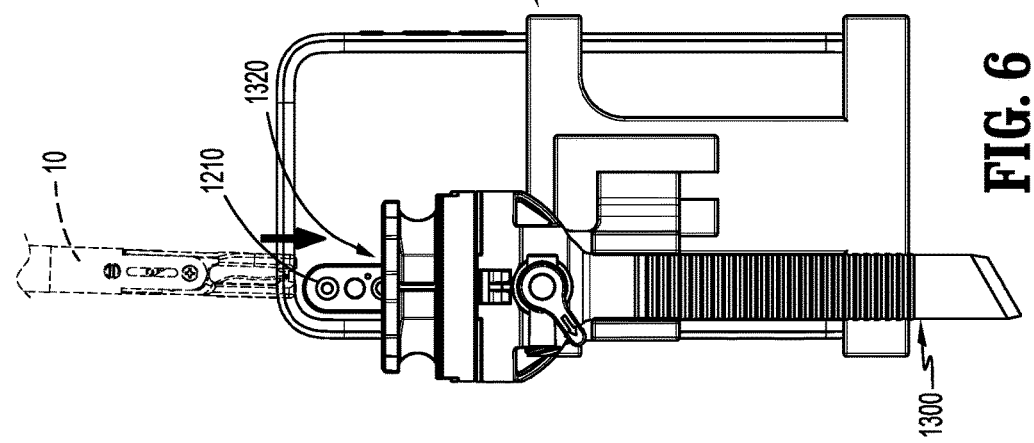
FIG. 6 is an end view of the monitoring system and cannula of FIG. 1 prior to insertion of an instrument into the cannula.

With additional reference to FIGS. 2 and 3, the mounting assembly 1100 of the monitoring system 1000 is configured to maintain the recording device 1200 relative to the cannula assembly 1300 to provide a constant view of an opening in the cannula assembly 1300 during insertion and removal of a surgical instrument 10 through the cannula assembly 1300 (FIGS. 6-8). Although shown and described with reference to the recording device 1200 having at least one camera 1210 and the cannula assembly 1300, the devices of the present disclosure may be modified for use with other digital or analog recording devices and/or with alternative cannula assemblies or surgical access devices.

The mounting assembly 1100 of the monitoring system 1000 includes a support member 1110 and a cradle member 1120. Although shown as two separate parts and as being releasably secured to one another, the support member 1110 and the cradle member 1120 may be integrally formed (i.e., monolithic) or fixedly secured to one another. The support member 1110 includes a first end 1111 including an engaging portion 1113 configured to engage the cannula assembly 1300 and a second end 1112 including a connecting portion 1115 configured to be releasably secured to the cradle member 1120. Optionally, and as shown, the mounting assembly 1100 further includes at least one dowel pin 1130.

The support member 1110 of the mounting assembly 1100 is operably connected to the engaging portion 1113 and the connecting portion 1115. The support member 1110 includes an elongated body 1116 having a substantially rectangular shape. Although shown and described as being integrally formed, it is envisioned that either or both of the engaging portion 1113 and the connecting portion 1115 may be separate components of the support member 1110. For example, it may be desired to have the engaging portion 1113 releasably connected to the support member 1110 to accommodate the cannula assemblies of different configurations. In embodiments, the cradle member 1120 could be exchanged for a different cradle member to accommodate a different recording device.

The engaging portion 1113 of the support assembly 1110 of the mounting assembly 1100 is configured to operably connect to the cannula assembly 1300. The engaging portion 1113 of the support assembly 1110 extends away from elongated body 1116 and includes a housing engaging portion 1113h configured to connect to a housing assembly 1310 of the cannula assembly 1300, and a cannula engaging portion 1113c configured to engage a tubular member 1330 of the cannula assembly 1300.

The housing engaging portion 1113h defines a first channel 1119a (FIG. 3), and the cannula engaging portion 1113c defines a second channel 1119b. The engaging portion 1113 may include an alignment feature (not shown) configured for passage through a portion of the cannula assembly 1300. For example, the engaging portion 1113 may include elements similar to a first protrusion 1117, shown in FIG. 3. The first protrusion 1117 extends away from the housing engaging portion 1113h and may include an elongated body with a triangular cross-sectional shape. Additionally, the first protrusion 1117 can be configured to engage an opening of the cannula assembly 1300 such as opening 1340. As shown, the mounting assembly 1100 includes two first protrusions 1117 disposed parallel one to another and defining the first channel 1119a. The first channel 1119a is configured to receive the housing assembly 1310.

The cannula engaging portion 1113c of the support member 1110 is configured to engage the tubular member 1330 of the cannula assembly 1300. For example, the cannula engaging portion 1113c can be configured to form a press-fit connection with the tubular member 1330. As shown, the cannula engaging portion 1113c includes two protrusions 1118 disposed parallel one to another and defining the second channel 1119b. The second channel 1119b is U-shaped and is configured to receive the tubular member 1330 therein. The second protrusions 1118 may be parallel to the first protrusions 1117. As shown, the second protrusions 1118 are rectangular and extend away from the engaging portion 1113.

Figure 4:
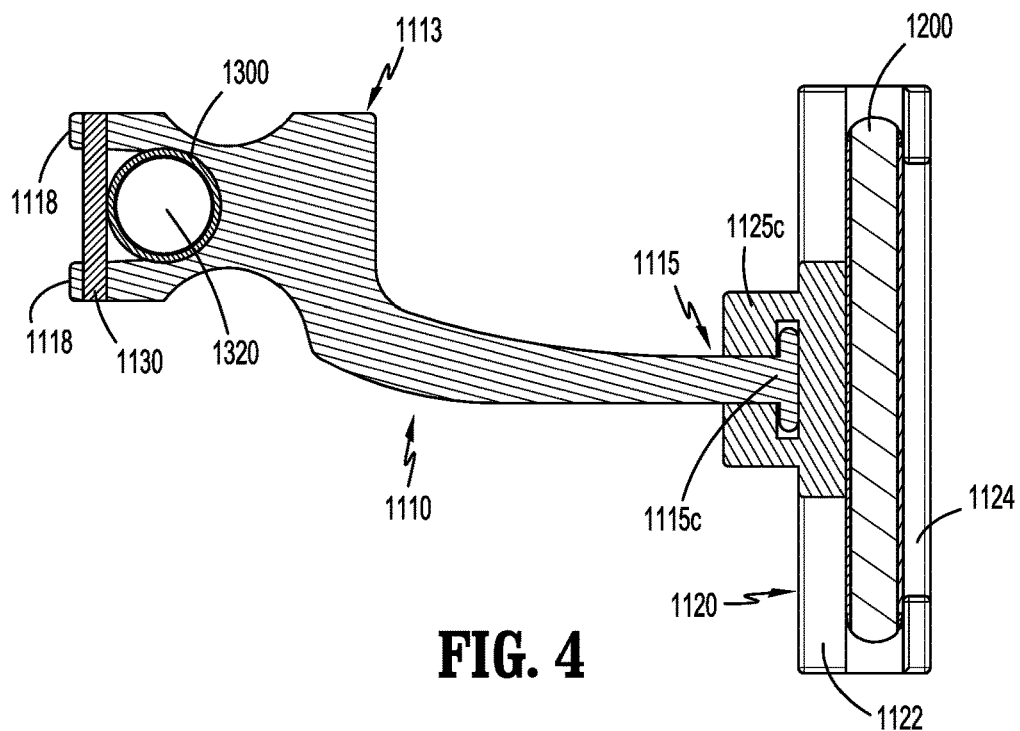
FIG. 4 is a cross-sectional side view of the monitoring system of FIG. 1, taken along line 4-4 shown in FIG. 2.
Figure 5:
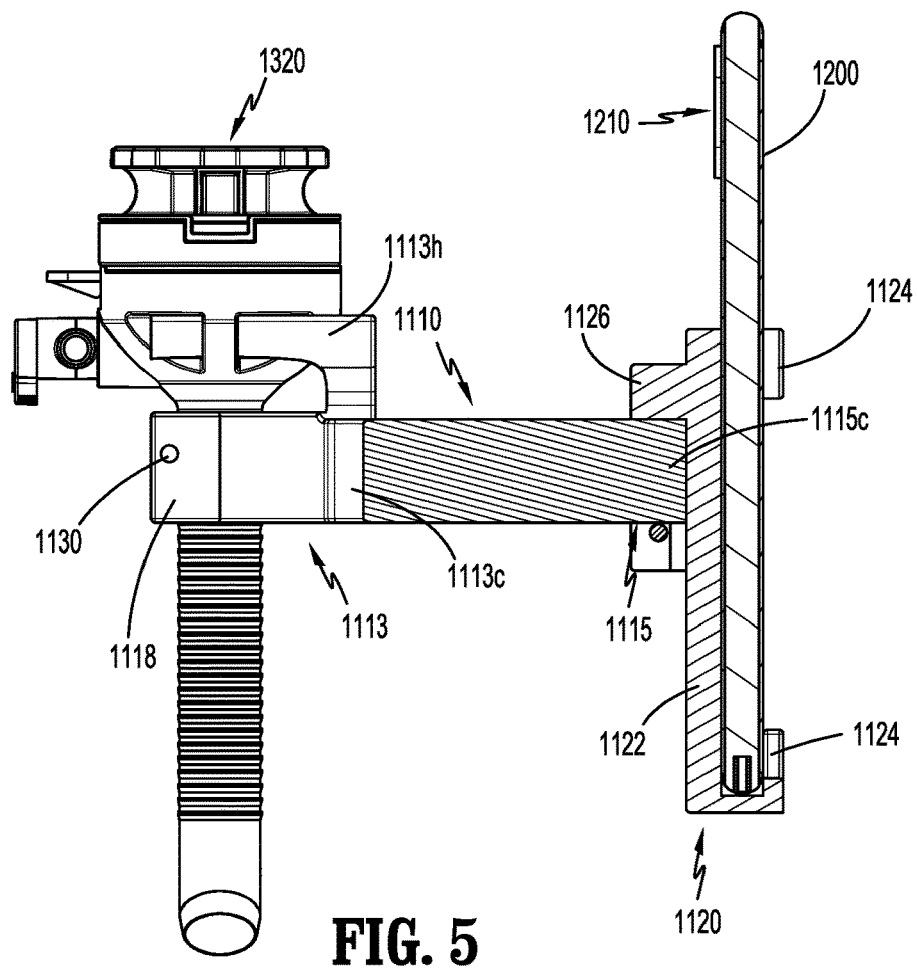
FIG. 5 is a side cross-sectional view of the monitoring system of FIG. 2, taken along section line 5-5.

As shown, the connecting portion 1115 of the support member 1110 is integrally formed (i.e., monolithically formed) with the support member 1110. As noted above, the connecting portion 1115 of the support member 1110 is configured to connect to the cradle member 1120. For example, the connecting portion 1115 of the mounting assembly 1100 includes a first connection member 1115c for releasably connecting the cradle member 1120 to the support member 1110. Alternatively, the first connection member 1115c of the connecting portion 1115 may be configured to releasably connect to a second connection member 1125c of the cradle member 1120. For example, as shown in FIGS. 3-5, the first connection member 1115c can be configured as a male connector (e.g., a slider) configured to slide into a second connection member 1125c configured as a female connector (e.g., slider-receiver). The first connection member 1115c corresponds to the second connection member 1125c. As shown, first connection member 1115c is a T-shaped member (FIG. 4) configured for pressed fitting into the second connection member 1125c. The second connection member 1125c defines a T-shaped channel (FIG. 4) and includes a stopping portion 1126 (FIGS. 3 and 5) configured to limit movement of the first connection member 1115c through the second connection member 1125c. The second connection member 1125c may be integrally formed (i.e., monolithic) with the cradle member 1120 or operably attached to the cradle member 1120. The connecting portion 1115 may be operably connected to the support member 1110.

The cradle member 1120 is configured to receive the recording device 1200. For example, the cradle member 1120 includes a cradle body 1122 (FIGS. 4 and 5), and engaging elements 1124 configured to keep the recording device 1200 engaged to the cradle member 1120. As shown in FIGS. 4 and 5, the engaging elements 1124 are L-shaped tabs that protrude away from cradle body 1122 of the cradle member 1120.

The recording device 1200 may be a digital camera, smartphone or any other device that includes at least one camera or other video recording mechanism. The recording device 1200 may be a recording device capable of recording video at a high frame rate. As shown, the recording device 1200 is configured for recording the speeds of insertion and removal of surgical instruments such as surgical instrument 10 (FIGS. 6-8) through the opening 1320 in the cannula assembly 1300.

Moreover, it may be desired to have the mounting assembly 1100 further configured as to include additional mechanisms or features that are configured to securely fix the connection between the cannula assembly 1300 and the recording device 1200 to the mounting assembly 1100. For example, the mounting assembly 1100 may include at least one opening 1140 (e.g., openings 1140a and 140b) configured to receive the dowel pin 1130. As shown, to maintain engagement between the cannula assembly 1300 and the engaging portion 1113, the mounting assembly 1100 includes openings 1140a (FIG. 3) which are configured to receive the dowel pin 1130. Moreover, to maintain engagement between the second connection member 1125c and the cradle member 1120, the mounting assembly 1100 includes openings 1140b (FIG. 3) which are configured to receive the dowel pin 1130. By positioning the dowel pin 1130 through the openings 1140a, the relative positions of the support member 1110 and the cannula assembly 1300 are maintained. Similarly, positioning the dowel pin 1130 through openings 1140b maintains the relative positions of the support member 1110 and the cradle member 1120.

FIGS. 5-8 illustrate the mounting assembly 1100 holding the recording device 1200 in alignment within the cannula assembly 1300. The mounting system 1100 is configured to retain the recording device 1200 relative to the cannula assembly 1300 while providing a constant view of the cannula assembly 1300 during insertion and removal of the surgical instrument 10 through the cannula assembly 1300. For example, the recording device 1200 may be positioned in such a way that enables recording the speed of insertion, removal, and/or manipulation of the surgical instrument 10 through the cannula assembly 1300 while passing within a field of view/recording of the recording device 1200. In another example, once the cannula assembly 1300 is properly engaged with the mounting assembly 1100, proper alignment of the cannula assembly 1300 with the recording device 1200 is ensured when the one camera 1210 of the recording device 1200 is aligned with an opening of the cannula assembly 1300, such as opening 1320.

Persons skilled in the art will understand that the devices and methods specifically described herein and illustrated in the accompanying drawings are non-limiting aspects of the present disclosure. It is envisioned that the elements and features illustrated or described in connection with the exemplary aspects may be combined with the elements and features of another without departing from the scope of the disclosure. As well, one skilled in the art will appreciate further features and advantages of the disclosure based on the above-described aspects. Accordingly, the disclosure is not to be limited by what has been particularly shown and described, except as indicated by the appended claims.

What is claimed is:

1. A monitoring system comprising:
    a recording device;
    a cannula assembly including a housing and a cannula extending from the housing; and
    a mounting system for aligning the recording device with the housing of the cannula assembly, the mounting system including:
        a cradle member configured to releasably retain the recording device; and
        a support member including an elongate body having a first end and a second end, the first end including a connecting portion for connecting the cradle member to the support member and the second end including an engaging portion for securing the support member to the cannula assembly.

2. The monitoring system of claim 1, wherein the recording device is configured to monitor insertion and removal of a surgical instrument through the cannula assembly.

3. The monitoring system of claim 2, wherein a camera of the recording device is aligned with an opening in the housing of the cannula assembly such that the opening in the housing of the cannula assembly is disposed within a field of view of the camera.

4. The monitoring system of claim 3, wherein the camera and the opening in the housing of the cannula assembly are perpendicularly aligned.

5. The monitoring system of claim 1, wherein the connecting portion includes a first connection member configured to releasably connect to a second connection member.

6. The monitoring system of claim 5, wherein the first connection member is a male connector and the second connection member is a female connector configured to receive the male connector.

7. The monitoring system of claim 6, wherein the male connector is a T-shaped slider.

8. The monitoring system of claim 7, wherein the T-shaped slider is retained within a channel of the female connector between a stopper and a dowel pin.

9. The monitoring system of claim 1, wherein at least a portion of the engaging portion is configured to snap onto a portion of the cannula assembly or to frictionally receive at least a portion of the cannula assembly.

10. The monitoring system of claim 1, wherein the engaging portion includes a housing engaging portion and a cannula engaging portion, the housing engaging portion being configured to engage a housing of the cannula assembly and the cannula engaging portion being configured to engage the cannula of the cannula assembly.

11. The monitoring system of claim 1, wherein the engaging portion includes at least one protrusion configured to engage the cannula assembly.

12. The monitoring system of claim 1, wherein the engaging portion defines at least one channel configured to engage the cannula of the cannula assembly.

13. The monitoring system of claim 12, wherein the at least one channel is U-shaped.

14. A monitoring system comprising:
    a cannula assembly including a housing and a cannula extending from the housing; and
    a mounting system for aligning a recording device with the housing of the cannula assembly, the mounting system including:
        a cradle member configured to releasably retain the recording device; and
        a support member including an elongate body having a first end and a second end, the first end including a connecting portion for connecting the cradle member to the support member, and the second end including an engaging portion for securing the support member to the cannula assembly.

15. The monitoring system of claim 14, wherein the mounting system is configured to align a camera of the recording device with an opening in the housing of the cannula assembly.

16. The monitoring system of claim 14, wherein the connecting portion includes a first connection member and the cradle member includes a second connection member, the first connection member being configured to releasably connect to the second connection member.

17. The monitoring system of claim 16, wherein the first connection member is a male connector and the second connection member is a female connector configured to receive the male connector.

18. The monitoring system of claim 17, wherein the male connector is a T-shaped slider.

19. The monitoring system of claim 14, wherein at least a portion of the engaging portion is configured to snap onto a portion of the cannula of the cannula assembly or to frictionally receive at least a portion of the cannula of the cannula assembly.

20. A mounting system comprising:
a cradle member configured to releasably retain a recording device; and
a support member for aligning the recording device with a housing of a cannula assembly, the support member including an elongate body having a first end and a second end, the first end including a connecting portion for connecting the cradle member to the support member, and the second end including an engaging portion for securing the support member to the cannula assembly.

* * * * *